(12) United States Patent
Kiessling et al.

(10) Patent No.: US 6,538,072 B2
(45) Date of Patent: Mar. 25, 2003

(54) METHODS FOR MAKING MULTIVALENT ARRAYS

(75) Inventors: Laura L. Kiessling, Madison, WI (US); Laura E. Strong, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/888,098

(22) Filed: Jun. 22, 2001

(65) Prior Publication Data

US 2002/0007016 A1 Jan. 17, 2002

Related U.S. Application Data

(62) Division of application No. 09/335,430, filed on Jun. 17, 1999, now Pat. No. 6,271,315.

(51) Int. Cl.⁷ .............. C08F 8/30; C08F 4/26; C08F 8/34; C08F 8/40
(52) U.S. Cl. .............. 525/326.1; 525/326.7; 525/326.8; 525/327.2; 525/327.5; 525/327.6; 525/327.7; 525/328.5; 525/328.8; 525/328.9; 525/340; 525/342; 525/343; 525/379; 525/384; 525/385; 525/386; 526/172; 526/199; 526/200
(58) Field of Search .................. 525/326.1, 326.7, 525/326.8, 327.2, 327.5, 327.6, 327.7, 328.5, 328.8, 328.9, 340, 342, 343, 379, 384, 385, 386; 526/172, 199, 200

(56) References Cited

U.S. PATENT DOCUMENTS

| | | | |
|---|---|---|---|
| 4,883,851 A | 11/1989 | Grubbs et al. | 526/268 |
| 5,100,972 A | 3/1992 | Sivavec et al. | 525/391 |
| 5,312,940 A | 5/1994 | Grubbs et al. | 556/136 |
| 5,342,909 A | 8/1994 | Grubbs et al. | 526/171 |
| 5,587,442 A | 12/1996 | Kiessling et al. | 526/238.2 |
| 5,710,298 A | 1/1998 | Grubbs et al. | 556/22 |
| 5,750,815 A | 5/1998 | Grubbs et al. | 585/511 |
| 5,831,108 A | 11/1998 | Grubbs et al. | 556/21 |
| 5,849,851 A | 12/1998 | Grubbs et al. | 526/93 |
| 5,880,231 A | 3/1999 | Grubbs et al. | 526/171 |
| 5,889,128 A | 3/1999 | Schrock et al. | 526/107 |
| 5,969,170 A | * 10/1999 | Grubbs et al. | 556/21 |
| 6,080,826 A | * 6/2000 | Grubbs et al. | 526/75 |
| 6,291,616 B1 | 9/2001 | Kiessling et al. | 526/171 |

OTHER PUBLICATIONS

Albagli, D. et al., "New Functional Polymers Prepared by Ring–Opening Methathesis Polymerization: Study of the Quenching of Luminescence of Pyrene End Groups by Ferrocene or Phenothiazine Centers in the Polymers," *J. Phys. Chem.*, 97(39):10211–10216 (1993).*

Albagli, D. et al., "Surface Attachment of Well–Defined Redox–Active Polymers and Block Polymers via Terminal Functional Groups," *J. Am. Chem. Soc.*, 115(16):7328–7334 (1993).*

Biagini, S.C.G. et al., "Synthesis of Penicillin Derived Polymers Utilizing Ring–Opening Metathesis Polymerization Methodology," *Chem. Commun.*, 1097–1098 (1997).*

(List continued on next page.)

*Primary Examiner*—David W. Wu
*Assistant Examiner*—R. Harlan
(74) *Attorney, Agent, or Firm*—Greenlee, Winner and Sullivan, P.C.

(57) ABSTRACT

A method of preparing a multivalent array that includes: polymerizing at least one monomer comprising at least one polymerizable group and at least one latent reactive group in the presence of a metal carbene catalyst to form a polymer template comprising at least one latent reactive group; and combining the polymer template with at least one functionalizing reagent comprising at least one reactive group under conditions effective to react the latent reactive group of the polymer template with the reactive group of the functionalizing reagent to form a multivalent array.

5 Claims, 6 Drawing Sheets

OTHER PUBLICATIONS

Biagini, S.C.G. et al., "Living Ring–Opening Metathesis Polymerization of Amino Ester Functionalized Norbornenes," *Polymer, 39(5)*:1007–1014 (1998).*

Buerke, M. et al., "Sialyl Lewis*–containing Oligosaccharide Attenuates Myocardial Reperfusion Injury in Cats," *J. Clin. Invest., 93:*1140–1148 (1994).*

Cannizzo, L.F. et al., "End Capping of Polynorbornene Produced by Titanacyclobutanes," *Macromolecules, 20(7)*:1488–1490 (1987).

Chernyak, A.Y. et al., "Synthesis of Lysine–Containing Fragments of the *Proteus Mirabilis* O27 O–Specific Polysaccharide and Neoglyco–conjugates Therefrom," *Carbohyd. Res., 225:*279–289 (1992).

Del Rio, I. et al., "Ring–Opening Metathesis Polymerization of Norbornene Catalyzed by a Ru(II)–Vinylidene Complex," *Tetrahedron Lett., 40:*1401–1404 (1999).

Dias, E.L. et al., "Well–Defined Ruthenium Olefin Metathesis Catalysts: Mechanism and Activity," *J. Am. Chem. Soc., 119(17)*:3887–3897 (1997).

Dias, E.L. et al., "Synthesis and Investigation of Homo– and Heterobimetallic Ruthenium Olefin Metathesis Catalysts Exhibiting Increased Activities," *Organometallics, 17(13)*:2758–2767 (1998).

Furstner, A. et al. "A Most User–Friendly Protocol for Ring Closing Metathesis Reactions," *Chem. Commun.,* 95–96 (1999).

Gibson, V.C. et al., "Thymine Functionalized Polymers Via Living Ring–Opening Metathesis Polymerisation," *Chem. Commun.,* 1095–1096 (1997).

Goldstein, T.J. et al., "Carbohydrate Binding Specificity of Concanavalin A" Chapter 4, in *Concanavalin A as a Tool;* H. Bittiger and H. P. Schnebli, Ed., John Wiley & Sons. Ltd.: London, 1976, Coll., pp. 55–65.

Gordon, E.J. et al., "Glycoprotein–Inspired Materials Promote the Proteolytic Release of Cell Surface L–Selectin," *Bioorg. Med. Chem., 6:*1293–1299 (1998).

Gordon, E.J. et al., "Synthetic Ligands Point to Cell Surface Strategies," *Nature, 392:*30–31 (1998).

Grubbs, R.H., "The Development of Functional Group Tolerant Romp Catalysts," *J.M.S. Pure Appl. Chem., A31(11)*:1829–1833 (1994).

Hillmyer, M.A. et al., "Ring–Opening Metathesis Polymerization of Functionalized Cyclooctenes by a Ruthenium–Based Metathesis Catalyst," *Macromolecules, 28(18)*:6311–6316 (1995).

Ivin, K.J. et al., Chapter 11, "Ring–Opening Metathesis Polymerization: General Aspects," *Olefin Metathesis and Metathesis Polymerization;* Academic Press: San Diego, CA, pp. 224–259 (1997).

Kanai, M. et al., "Varying the Size of Multivalent Ligands: The Dependence of Concanavalin A Binding on Neoglycopolymer Length," *J. Am. Chem. Soc., 119:* 9931–9932 (1997).

Kiessling, L.L. et al., "Bioactive Polymers," in *Topics in Organometallic Chemistry, vol. 1: Alkene Metathesis in Organic Synthesis* A. Furstner. Ed. Springer (1998) pp. 199–231.

Kiessling, L.L., NIH Grant Abstract No. 5R01GM55984–03 entitled "Multivalent Protein Carbohydrate Interactions" Jun. 1, 1997.

Kingery–Wood J.E. et al., "The Agglutination of Erythrocytes by Influenza Virus is Strongly Inhibited by Liposomes Incorporating an Analog of Sialyl Gangliosides," *J. Am. Chem. Soc., 114(18)*:7303–7305 (1992).

Kingsbury, J.S. et al., "A Recyclable Ru–Based Metathesis Catalyst," *J. Am. Chem. Soc., 121(4)*:791–799 (1999).

Lee, R.T. et al., "Synthesis of 3–(2–Aminoethylthio)Propyl Glycosides," *Carbohyd. Res., 37:* 193–201 (1974).

Lynn, D.M. et al., "Living Ring–Opening Metathesis Polymerization in Aqueous Media Catalyzed by Well–Defined Ruthenium Carbene Complexes," *J. Am. Chem. Soc., 118(4)*:784–790 (1996).

Mann, D.M. et al., "Probing Low Affinity and Multivalent Interactions with Surface Plasmon Resonance: Ligands for Concanavalin A," *J. Am. Chem. Soc., 120(41)*:10575–10582 (1998).

Manning, D.D. et al., "Neoglycopolymer Inhibitors of the Selectins," *Tetrahedron, 53(35)*:11937–11952 (1997).

Mortell, K.H. et al., "Recognition Specificy of Neoglycopolymers Prepared by Ring–Opening Metathesis Polymerization," *J. Am. Chem. Soc., 118(9)*:2297–2298 (1996).

Mortell, K.H. et al., "Synthesis of Cell Agglutination Inhibitors by Aqueous Ring–Opening Opening Metathesis Polymerization," *J. Am. Chem. Soc.,* 116(26):12053–12054 (1994).

Osawa, T. et al., "Gorse (*Ulex europeus*) Phytohemagglutinins," *Methods Enzymol., 28:*323–327 (1972).

Roy,R. et al., "Custom–Designed Glycopolymer Syntheses by Terpolymerizations," *J. Chem. Soc., Chem. Commun.,* No. 21, 1611–1613 (1992).

Roy, R. et al., "Solid–Phase Synthesis of Dendritic Sialoside Inhibitors of Influenza A Virus Haemagglutinin," *J. Chem. Soc., Chem. Commun.,* 1869–1872 (1993).

Sanders, W.J. et al., "Inhibition of L–Selectin–Mediated Leukocyte Rolling by Synthetic Glycoprotein Mimics," *J. Biol. Chem., 274:*5271–5278 (1999).

Schnaar, R.L. et al., "Preparation of Polyacrylamide Gels Containing Active Esters," *Methods in Enzymology, 83:* 306–310 (1982).

Scholl, M. et al., "Increased Ring Closing Metathesis Activity or Ruthenium–Based Olefin Metathesis Catalysts Coordinated with Imidazolin–2–ylidene Ligands," *Tetrahedron Lett., 40:* 2247–2250 (1999).

Schrock, R.R. et al., "Synthesis of Molybdenum Imido Alkylidene Complexes and Some Reactions Involving Acyclic Olefins," *J. Am. Chem. Soc., 112(10)*:3875–3886 (1990).

Schwab, P. et al., "Synthesis and Applications of RuCl$_2$(=CHR')(PR$_3$)$_2$: The Influence of the Alkylidene Moiety on Metathesis Activity," *J. Am. Chem. Soc., 118(1)*:100–110 (1996).

Schwab, P. et al., "A Series of Well–Defined Metathesis Catalyst– Synthesis of [RuCl$_2$(=CHR')(PR$_3$)$_2$] and Its Reactions," *Angew. Chem. Int. Ed. Engl., 34:* 2039–2041 (1995).

Spaltenstein, A. et al., "Polyacrylamides Bearing Pendant – Sialoside Groups Strongly Inhibit Agglutination of Erythrocytes by Infleunza Virus," *J. Am. Chem. Soc., 113:*687–688 (1991).

Sparks M.A. et al., "Neuraminidase–Resistant Hemagglutination Inhibitors: Acrylamide Copolymers Containing a C–Glycoside of N–Acetylneuraminic Acid," *J. Med. Chem., 36(6)*:778–783 (1993).

Spevak, W. et al., "Polymerized Liposomes Containing C–Glycosides of Sialic Acid; Potent Inhibitors of Influenza Virus in Vitro Infectivity," *J. Am. Chem. Soc., 115:* 1146–1147 (1993).

Still, W.C., "Rapid Chromatographic Technique for Preparative Separations with Moderate Resolution," *J. Org. Chem., 43(14)*:2923–2925 (1978).

Varki, A., "Selectin Ligands," *Proc. Natl. Acad. Sci. USA, 91:* 7390–7397 (1994).

Ver Nooy, C.D. et al., "Formation of Nortricyclene Derivatives by Bromination of exo–2,5–Methylene–1,2,5,6–tetrahydrobenzoic Acids," *J. Am. Chem. Soc., 77:* 3583–3586 (1955).

Weck, M. et al., "Ring–Opening Metathesis Polymerization from Surfaces," *J. Am. Chem. Soc., 121(16)*:4088–4089 (1999).

Weskamp, T. et al., "A Novel Class of Ruthenium Catalysts for Olefin Metathesis," *Angew., Int. Ed. Engl., 37:* 2490–2493 (1998).

* cited by examiner

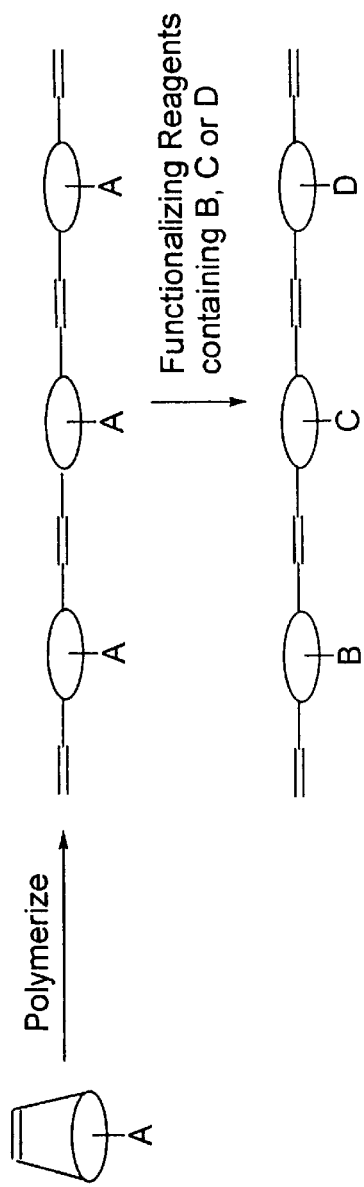
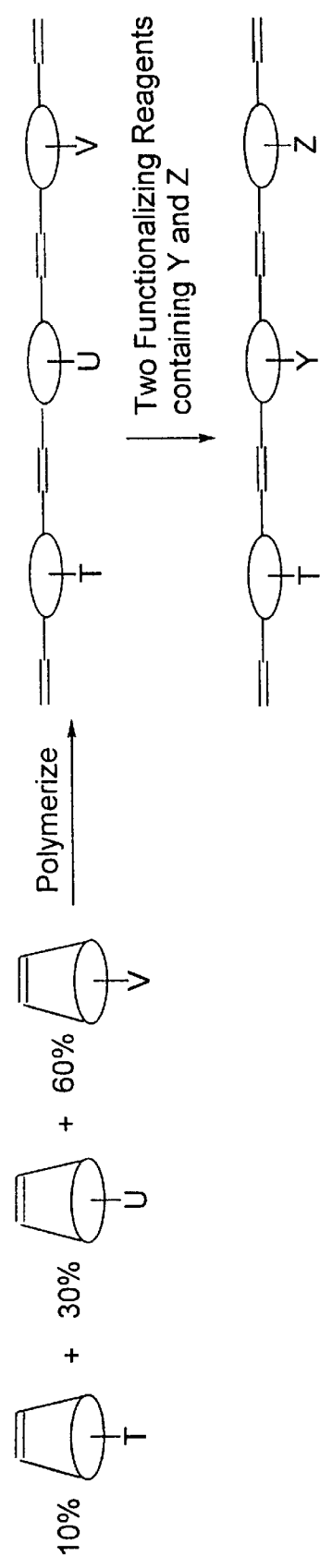
FIG. 1A
FIG. 1B

Post-Synthetic Modification

Emulsion Conditions

METHODS FOR MAKING MULTIVALENT ARRAYS

CROSS-REFERENCE TO RELATED APPLICATIONS

This application is a division of U.S. patent application Ser. No., 09/335,430, filed on Jun. 17, 1999, now U.S. Pat. No. 6,271,315, which is incorporated in its entirety by reference herein.

STATEMENT OF GOVERNMENT RIGHTS

The present invention was made with United States government support awarded by the following agency, NIH GM55984. The United States has certain rights in this invention.

BACKGROUND OF THE INVENTION

New materials and methods of synthesis are emerging as significant areas of research. They have applications in the fields of biotechnology, medicine, pharmaceuticals, medical devices, polymers, etc. The ring-opening metathesis polymerization (ROMP) method has emerged as a powerful synthetic method for the creation of such useful materials. Many examples in which ROMP has been used to generate functionalized materials have focused on the incorporation of pendant functionality into the monomers, thereby forming a multivalent array. As used herein, a multivalent array refers to a polymer (random or block of varying lengths, including shorter oligomers) having pendant functional groups that impart various properties to the polymer. Such multivalent arrays are also often referred to as multivalent ligands, multivalent displays, multidentate arrays, multidentate ligands, or multidentate displays.

Such multivalent arrays are particularly useful in the medical and biotechnology areas. For example, the binding of cell surface receptors to particular epitopes of multivalent arrays can trigger a wide variety of biological responses. Such multivalent binding events have unique consequences that are dramatically different than those elicited by monovalent interactions. For instance, signaling through the epidermal growth factor is promoted by the binding of divalent ligands, which apparently promote dimerization of the transmembrane receptor, yet monovalent ligands also bind the receptor but produce no signal. In addition, multivalent arrays have been shown to induce the release of a cell surface protein, suggesting a new mechanism for controlling protein display. In protein-carbohydrate recognition processes, multivalent saccharide-substituted arrays can exhibit increased avidity, specificity, and unique inhibitory potencies under dynamic conditions of shear flow. Thus, the ability to synthesize defined, multivalent arrays of biologically relevant binding epitopes provides a means for exploring and manipulating physiologically significant processes.

Because they can span large distances, linear multivalent arrays of varying length and epitope density are particularly useful for probing structure-function relationships in biological systems. Chemical and chemoenzymatic routes have been developed for the generation of di- and trivalent ligands, dendrimers, and high molecular weight polymers, but well defined, linear oligomers have proven more difficult to synthesize. Thus, what is needed is a general strategy to create diverse arrays of different multivalent materials of varying length.

One way in which this could be done is through the use of ROMP technology. ROMP has been used to generate defined, biologically active polymers (Gibson et al., *Chem. Commun.*, 1095–1096 (1997); Biagini et al., *Chem. Commun.*, 1097–1098 (1997); Biagini et al., *Polymer*, 39, 1007–1014 (1998); and Kiessling et al., *Topics in Organometallic Chemistry*, 1, 199–231 (1998)) with potent and unique activities that range from inhibiting protein-carbohydrate recognition events to promoting the proteolytic release of cell surface proteins (Mortell et al., *J. Am. Chem. Soc.*, 118, 2297–2298 (1996); Mortell et al., *J. Am. Chem. Soc.*, 116, 12053–12054 (1994); Kanai et al., *J. Am. Chem. Soc.*, 119, 9931–9932 (1997)); Kingsbury et al., *J. Am. Chem. Soc.*, 121, 791–799 (1999); Schrock et al., *J. Am. Chem. Soc.*, 112, 3875–3886 (1990); Gordon et al., *Nature*, 392, 30–31 (1998); and Sanders et al., *J. Biol. Chem.*, 274, 5271–5278 (1999)). The assembly of multivalent materials by ROMP has several advantages over classical methods for generation of multivalent displays. Specifically, ROMP can be performed under living polymerization conditions, and if the rate of initiation is faster than that of propagation, varying the monomer to initiator ratio (M:I) can generate materials of defined length (Ivin, *Olefin Metathesis and metathesis polymerization;* Academic Press: San Diego, 1997). This approach has been successfully applied with the Grubb's ruthenium metal carbene catalyst ($[(Cy)_3P]_2Cl_2Ru\!=\!CHPh$) to generate materials with narrow polydispersities, indicating that the resulting substances are fairly homogeneous (Dias et al., *J. Am. Chem. Soc.*, 119, 3887–3897 (1997); Lynn et al., *J. Am. Chem. Soc.*, 118, 784–790 (1996)). In contrast to anionic and cationic polymerization catalysts, ruthenium metal carbene initiators are tolerant of a wide range of functional groups.

There are, however, inherent disadvantages in the use of standard approaches that rely on ROMP to assemble biologically active materials. For example, the desired pendant functionality is incorporated into the monomers. Thus, a new functionalized cyclic olefin monomer, typically a functionalized bicyclic monomer, must be synthesized for each new polymer class to be produced. Also, the physical properties of each monomer, such as its solubility and the electron density and strain of the cyclic olefin, result in different rates of initiation, propagation, and non-productive termination of the reaction (Kanai et al., *J. Am. Chem. Soc.*, 119, 9931–9932 (1997)). In addition, purification of the desired products can be complicated depending on the structure of the monomer used.

Expedient, large-scale syntheses of multivalent arrays are hindered by these technical complications. Thus, what is needed is a general method for synthesizing multivalent arrays that addresses one or more of these issues. Ultimately, both large-scale production and the generation of libraries of oligomers would be facilitated by such a method.

SUMMARY OF THE INVENTION

The present invention provides methods for synthesizing multivalent arrays, such as functionalized polymers (herein, included within this term are relatively short oligomers). Significantly, the methods of the present invention can provide access to a wider range of materials with significant functions. For example, they can be used to generate libraries of oligomeric substances that differ in appended functionality as well as in length. Significantly, the methods of the present invention provide the ability to control the number and type of pendant functional groups. Such design control is important for elucidating structure/function relationships in biological systems, for example. The methods of the present invention can be used to produce random copolymers (i.e., polymers derived from two or more different monomers). In addition, block copolymers can be generated in which some blocks are held invariant while others are diversified through the method of the present invention. The blocks can vary in the backbone and/or the pendant functional groups.

In one embodiment, the present invention provides a method of preparing a multivalent array. The method includes: polymerizing at least one monomer comprising at least one polymerizable group and at least one latent reactive group in the presence of a metal carbene catalyst to form a polymer template comprising at least one latent reactive group; and combining the polymer template with at least one functionalizing reagent comprising at least one reactive group under conditions effective to react the latent reactive group of the polymer template with the reactive group of the functionalizing reagent to form a multivalent array. The monomer can optionally include functional groups nonreactive with the reactive group of the functionalizing reagent (herein, referred to as prefunctionalized monomers). In one embodiment, the latent reactive group of the monomer includes a nucleophilic group and the reactive group of the functionalizing reagent includes an electrophilic group. In another embodiment, the latent reactive group of the monomer includes an electrophilic group and the reactive group of the functionalizing reagent includes a nucleophilic group. In a particularly preferred embodiment, the electrophilic group is an activated ester group and the nucleophilic group is a primary amine group.

The polymer template, and hence, the multivalent array, can be a block copolymer or a random copolymer. A block copolymer is formed by the method described above wherein polymerizing at least one monomer comprises sequentially polymerizing two or more different monomers in the presence of a metal carbene catalyst to form a polymer template comprising alternating blocks of the different monomers. Alternatively, a random copolymer is formed by the method described above wherein polymerizing at least one monomer comprises simultaneously polymerizing two or more different monomers. Each different monomer can include a different latent reactive group for subsequent attachment of pendant functional groups. Such pendant functional groups can be derived from functionalizing reagents that react with the latent reactive group of the polymer template comprising a carbohydrate or a peptide.

The present invention also provides polymer templates and kits that include at least one polymer template. The kits also include instruction means for using a functionalizing reagent to attach a pendant functional group to the polymer template. The kits can also includes at least one functionalizing reagent and/or at least one capping agent.

BRIEF DESCRIPTION OF DRAWINGS

FIG. 1: Schematic of two synthetic routes for the formation of random copolymers.

DETAILED DESCRIPTION OF PREFERRED EMBODIMENTS

Figure 2A:
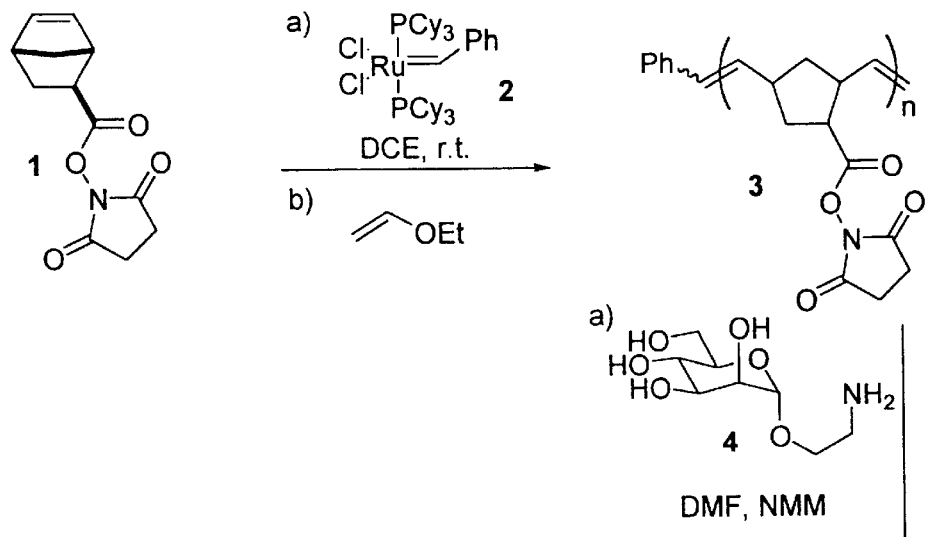
FIG. 2: Two synthetic routes used to generate the same multivalent mannose arrays. (A) An example of the method of the present invention involving polymerization of a nonpolar activated ester monomer template 1 followed by post synthetic modification of the resultant polymer template 3 with a carbohydrate recognition element 4. (B) An example of a conventional method involving polymerization of a carbohydrate-functionalized monomer 5 under emulsion conditions.

The present invention provides methods for synthesizing multivalent arrays. Preferably, the present invention provides general methods that can be used for both large-scale production and for the generation of libraries of oligomers, for example. Preferred embodiments of the present invention are significant because they are relatively high yielding, general, convenient, and/or efficient for the preparation of polymers of varying average lengths, varying epitope density, and varying functionality, for example. Of particular significance is the ability of the methods of the present invention to control the formation of arrays of varying length.

The methods of the present invention are based on the post-polymerization modification of a polymer backbone generated by a metal carbene-catalyzed ROMP system. In contrast to conventional methods that incorporate the desired pendant functional groups into the monomers, the methods of the present invention attach the desired pendant functional groups to preformed polymers. Significantly, the attachment of pendant functionality to preformed polymers generated by metal carbene-catalyzed ROMP provides better control and access to a wider variety of materials than previous methods were able to provide. Such materials may provide unique surfaces or ligands for a wide variety of natural and synthetic receptors.

Generally, the methods involve the use of a monomer and a ROMP metal carbene catalyst (also referred to as a metal carbene catalyst) to form an intermediate polymer (referred to herein as a polymer template). Preferably, the monomer and ROMP catalyst are sufficiently soluble in a common solvent, typically an organic solvent or mixture of solvents, to allow for the polymerization of the monomer, although the reaction can be carried out in the absence of a solvent (i.e., neat). Alternatively, more polar solvents such as water can be used if the metal carbene catalyst and the monomer are mutually soluble. The monomer includes in its structure at least one polymerizable group and at least one latent reactive group for subsequent attachment of a pendant functional group (i.e., subsequent functionalization). Thus, suitable latent reactive groups are those that are unreactive during the initial ROMP reaction but reactive during the subsequent functionalization (hence, the term "latent"). Examples of latent reactive groups include activated leaving groups such as an activated ester or protected functional groups such as a protected amine. As used herein, a "protected" group is one in which the intrinsic reactivity of the group is masked temporarily (i.e., the "mask" can be removed). Preferably, the monomer is a nonpolar monomer (i.e., one that is soluble in organic solvents), which can simplify isolation of the resultant polymer.

The resultant intermediate polymer acts as a template to which one or more functional groups can be appended using one or more functionalizing reagents that react with the latent reactive groups. In a typical reaction only one type of functional group is appended to a polymer template; however, by using less than stoichiometric amounts of several functionalizing reagents, several different functional groups can be appended to the polymer template. These functional groups may provide a recognition element (i.e., binding site) for a biological entity, such as a cell surface receptor. Alternatively, they may be generally unreactive (e.g., nonbinding to a cell surface receptor). Thus, the resultant polymers may be bioactive or biocompatible.

In the initial ROMP reaction, varying the ratio of monomer to ROMP catalyst (i.e., initiator) results in varying the length of the resultant polymer. Also in the initial ROMP reaction, different monomers can be used. A random copolymer can be made by polymerizing two or more different monomers. Each of the monomers can have different latent reactive groups for subsequent attachment of pendant functional groups. This is one way in which different pendant functional groups can be appended to the backbone, in addition to the method described above which depends on the addition of less than stoichiometric amounts of several functionalizing reagents. Alternatively, a block copolymer can be made by polymerizing a first monomer, adding a second monomer once the first monomer is completely consumed, etc. Another way in which to incorporate different pendant functional groups is to use a monomer that already includes a desired pendant functional group that requires no further functionalization, which is unreactive during the ROMP reaction, as is done in conventional ROMP methods (see, for example, Compound 5, FIG. 2, Route B). Using monomers with and without pendant functional groups provides additional advantage to the methods of the present invention.

A schematic of these various methods of making random polymers is shown in FIG. 1. In FIG. 1A, a single monomer is used to make a polymer template having the same latent reactive group (A) per repeat unit, to which less than stoichiometric amounts of three different functionalizing reagents (one containing functional group B, one containing functional group C, and one containing functional group D) are added to form a polymer having the same repeat unit in the backbone with different pendant functional groups (B, C, D). Alternatively, different monomers could be used, each with the same latent reactive group, to form a polymer template having different repeat units in the backbone but the same latent reactive groups. In FIG. 1B, different monomers, some of which have different latent reactive groups (U, V) and stable functional groups (T), are polymerized to form a polymer template having different repeat units and different latent reactive groups to which two different functionalizing reagents are added, either sequentially or simultaneously, to form a polymer having different repeat units in the backbone with different pendant functional groups (T, Y, Z).

Subsequent to the initial ROMP reaction and/or subsequent to the addition of pendant functional groups, the backbone of the polymer can be optionally modified for additional advantage. For example, the backbone can be reduced to eliminate double bonds (as through the use of a diimide) or oxidized to form hydroxyl groups (as through the use of $OsO_4$). Other alkene functionalization can also be incorporated into the backbone to yield desired materials.

Figure 2B:
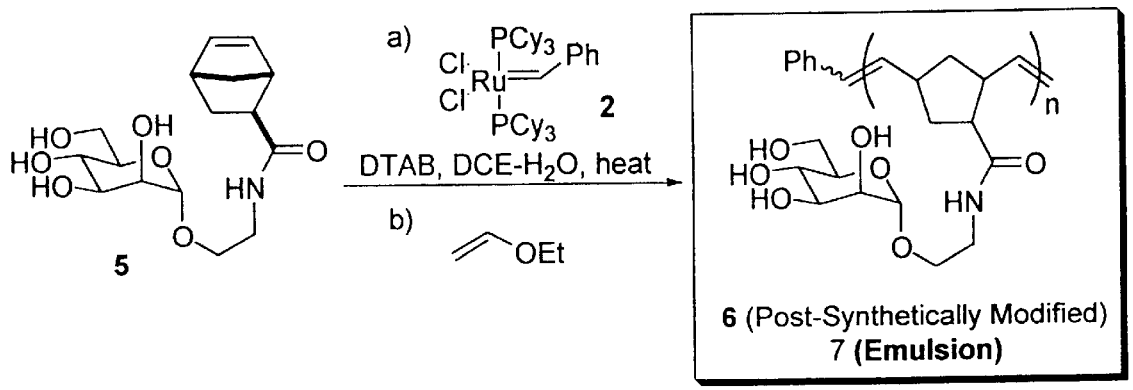

An example of one synthetic route according to the method of the present invention is shown in FIG. 2. In this example, multivalent mannose arrays are prepared. FIG. 2A shows an example of a method of the present invention involving polymerization of a nonpolar activated ester monomer 1 followed by post synthetic modification of the resultant polymer template 3 with a carbohydrate-containing functionalizing reagent 4. For comparison purposes, FIG. 2B shows an example of a conventional method involving polymerization of a carbohydrate-functionalized monomer 5 under emulsion conditions.

Suitable monomers for use in the methods of the present invention, having at least one polymerizable group (and often only one polymerizable group) and at least one latent reactive group (used for functionalization), that can be used to make a polymer template are those that are stable to the ROMP polymerization conditions. Preferably, suitable monomers are those that can be polymerized through ROMP under standard conditions. More preferably, the monomers include substituted cyclic (e.g., monocyclic, bicyclic, tricyclic, or higher order cyclics) mono-olefins. Examples include, but are not limited to, strained olefins such as norbornene, cyclobutene, and less strained olefins such as cyclooctene. Such substituted cyclic mono-olefins can also include heteroatoms and functional groups within the ring, including, for example, thioethers (RSR' or $R_2S$), ethers (ROR' or $R_2O$), amines (primary $RNH_2$; secondary RR"NH or $R_2NH$; tertiary RR'R"N or $R_2R'N$ or $R_3N$), amides (i.e. RCONHR'), and esters ($RCO_2R'$). Examples of such olefins include oxanorbornene, 7-thia-bicyclo[2.2.1]hept-2-ene, and 3,6,7,8-tetrahydro-1H-azocin-2-one, the structures of which are as follows:

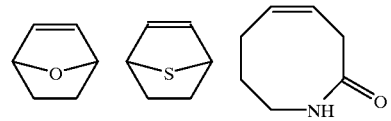

The latent reactive groups on the monomers that are used for functionalization include electrophilic or nucleophilic groups. Analogously, the compounds from which the pendant functional groups are derived (i.e., the functionalizing reagents) include electrophilic or nucleophilic groups. These two sets of groups may be the same or different, although for any two reactants (monomer and functionalizing reagent) the latent reactive groups are matched to allow for reaction and attachment of the pendant functional group to the polymer template.

Examples of electrophilic latent reactive groups include, but are not limited to, acyl sulfonamides ($RCONHSO_2R'$), acyl azides ($RCON_3$), epoxides (RR'COCR'R'''), anhydrides ($RCO_2COR'$), esters ($RCO_2R'$; including activated esters such as pentafluorophenyl esters and N-hydroxysuccinimidyl esters), carboxylic acids ($RCO_2H$; including activated acids such as acyl halides RCOX wherein X=Br, I, Fl, Cl), halides (F, Br, Cl, I), boronic acids and esters ($RB(OH)_2$; RB(OH)(OR"); $RB(OR')_2$), ketones (RCOR'), aldehydes (RCHO), phosphoric acid esters (mono-, di-, and triesters, such as $PO(OR)(OH)_2$; $PO(OR)_2$(OH); $PO(OR)_3$), phosphites ($POR_3$), acyl nitriles (RCOCN), alkenes (RR'CCR"R'''), alkynes (RCCR'), and the like. Examples of nucleophilic latent reactive groups include, but are not limited to, amines (primary $RNH_2$; secondary RR'NH or $R_2NH$; tertiary RR'R"N or $R_2R'N$ or $R_3N$), azides ($RN_3$), hydroxyls (ROH), thiols (RSH), sulfones ($R_2RSO_2$ or $RSO_2R'$), acyl hydrazides ($RCONHNH_2$), phosphites ($POR_3$), hydrazines ($RHNNH_2$), oximes (RHCNOH), isocyanates (RNCO), hydroxamic acids (RCONHOH), thiocyanates (RSCN), and the like. The stereochemistry of these groups may be defined or racemic. If desired these groups may be protected with groups such as carbamate (RNHCO$_2$R'), carbonate (ROCO$_2$R'), thioethers (RSR' or R$_2$S), disulfides (RSSR' or RSSR), nitro groups (RNO$_2$), and the like.

Suitable monomers may also include one or more appended groups that are not used for functionalization (i.e., nonreactive under the conditions of functionalization). Such groups include hydroxyls (ROH), alkyls, aryls, halides (F, Br, Cl, I), amides (RCONHR'), thiols (RSH), and the like. The stereochemistry of these groups may be defined or racemic. Although some of these groups are the same as the latent reactive groups, they are not as reactive under the conditions chosen for attachment of the pendant functional group and are referred to herein as stable functional groups. Thus, stable is used in this context as a relative term to refer to groups that are unreactive under the chosen conditions.

An example of a class of suitable monomers based on the norbornene ring structure has the following general structure:

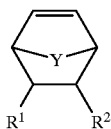

Formula I wherein Y is CH$_2$, O, S, or N—R$^3$ (wherein R$^3$ is H or an organic group), R$^1$ and R$^2$ may be H or an organic group, which may be connected such that they form a ring, with the proviso that at least one of R$^1$ and R$^2$ includes a latent reactive group as defined above, such as an activated ester. A specific example is bicyclo[2.2.1]hept-5-ene-exo-2-carboxylic acid N-hydroxysuccinimide ester (Compound 1, FIG. 2).

The monomers can be prepared using standard organic synthetic techniques known to one of skill in the art. For example, the monomer bicyclo[2.2.1]hept-5-ene-exo-2-carboxylic acid can be synthesized according to the procedure of Ver Nooy et al., *J. Am. Chem. Soc.*, 77, 3583–3586 (1955).

The polymer template is preferably prepared by polymerizing one or more monomers using a metal carbene catalyst (i.e., a compound containing a metal carbene, M=C—R$^4$R$^5$ group, wherein R$^4$ and R$^5$ are each independently H or an organic, which may include functionality such as latent reactive groups or nonreactive functional groups, and "M" represents a metal, which is bonded to one or more ligands in a ligand sphere). Specific examples include, but are not limited to, Grubb's ruthenium metal carbene catalyst (Compound 2, FIG. 2) and the compounds shown in FIG. 3 and disclosed in Kingsbury et al., *J. Amer. Chem. Soc.*, 121, 791–799 (1999); Schwab et al., *J. Amer. Chem. Soc.*, 118, 100–110 (1996); Dias et al., Organometallics, 17, 2758–2767 (1998); del Rio et al., *Tetrahedron Lett.*, 40, 1401–1404 (1999); Furstner et al., *Chem. Commun.*, 95–96 (1999); Schrock et al., *J. Amer. Chem. Soc.*, 112, 3875–3886 (1990); Weskamp et al., *Angew. Chem., Int. Ed Engl.*, 37, 2490–2493 (1998); and Scholl et al., *Tetrahedron Lett.*, 40, 2247–2250 (1999). Unique and preferred ruthenium and osmium catalysts that incorporate unique functionality are described in Applicants' Assignee's U.S. Pat. No. 6,291,616, filed on even date herewith entitled "Methods and Reagents for Capping Ruthenium or Osmium Carbene-Catalyzed ROMP Products."

The polymerization is preferably carried out in a solvent or mixture of solvents, typically one or more organic solvents, in which the monomer and catalyst are mutually soluble, although in certain embodiments, no solvent is required. Suitable solvents include substituted and unsubstituted aliphatic and aromatic hydrocarbon solvents such as chlorinated hydrocarbons, ethers, protic hydrocarbons, etc., which are unreactive under the reaction conditions. Examples include 1,2-dichloroethane, benzene, toluene, p-xylene, methylene chloride, dichlorobenzene, tetrahydrofuran, diethylether, pentane, etc. Alternatively, water may be used as the solvent if the monomer and catalyst are mutually soluble.

The conditions of the reaction (e.g., temperature, time, atmosphere) will vary depending on the choice of monomer and catalyst, and can be selected by one of skill in the art without undue experimentation. Preferably, the ROMP reaction is carried out at a temperature of about 20° C. to about 30° C. (i.e., room temperature) or higher under an inert atmosphere (e.g., nitrogen or argon), although temperatures ranging from about –20° C. to about 125° C. are possible. Pressure is not critical, but may be varied to maintain a liquid phase reaction mixture. Reaction times can vary from several minutes to several days. The polymer can be terminated with an appropriate capping agent when all the monomers have been completely consumed. The capping agent typically depends on the catalyst used. For example, for the Grubb's ruthenium metal carbene catalyst (Compound 2, FIG. 2), an electron rich alkene is used. As used herein, an electron rich alkene is one that has greater electron density than that of ethylene. In conventional capping methods, the capping agent is a vinyl ether, typically ethyl vinyl ether, that yields a material with a terminal alkene and a deactivated alpha-oxygen-substituted ruthenium metal carbene (Hillmyer et al., *Macromolecules*, 28, 6311–6316 (1995)). The electron rich alkene can be any of a variety of alkenes, such as a vinyl ether, an example of which is ethyl vinyl ether. For other metal carbene catalysts, aldehydes may be used. Examples of known capping agents can be found in the literature. Unique and preferred capping agents that incorporate unique functionality (latent reactive groups or nonreactive functional groups such as reporter groups to facilitate detection such as fluorescent groups, chemiluminescent groups, enzymes, antibodies, biotin, radioactive groups, etc.) are described in Applicants' Assignee's U.S. Pat. No. 6,291,616, filed on even date herewith entitled "Methods and Reagents for Capping Ruthenium or Osmium Carbene-Catalyzed ROMP Products." Alternative to a capping agent, the polymer template can be terminally functionalized by oxidizing the catalyst and forming an aldehyde at the terminus of the backbone of the polymer template. This is also described in greater detail in Applicants' Assignee's U.S. Pat. No. 6,291,616, filed on even date herewith entitled "Methods and Reagents for Capping Ruthenium or Osmium Carbene-Catalyzed ROMP Products." As stated above, the length of the polymer template is typically dependent on the ratio of monomer to initiator. This provides a very controllable mechanism by which to vary the length of the backbone of the multivalent array.

Typically, the polymer template has the following general structure:

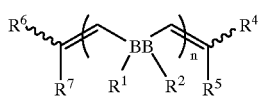

Formula II wherein "BB" represents the backbone repeat unit, which may be cyclic or acyclic, and may be the same or different in a random or block arrangement, $R^1$ and $R^2$ are as defined above, $R^4$ and $R^5$ are H or an organic group derived from the metal carbene catalyst (i.e., $R^4$ and $R^5$ are the substituents on the metal carbene carbon of the metal carbene catalyst, typically, phenyl and hydrogen if the Grubb's catalyst Compound 2, FIG. 2, is used), and $R^6$ and $R^7$ are H or an organic group, which is typically derived from the capping agent (e.g., $R^6$ and $R^7$ are the substituents on the alkene carbon of the electron rich alkene, such as hydrogen in the case of ethyl vinyl ether), and n is the average number of repeating monomer units, which can be varied by controlling the monomer to catalyst ratio. Typically, n is at least 2 and no more than about 10,000, but there is practically no limit. As discussed above, ROMP can provide polymers of varying average lengths (i.e., varying degree of polymerization, DP) depending on the monomer to ROMP catalyst (i.e., initiator) ratios. The length of all polymers described herein are referred to as the length predicted by the monomer to initiator ratio used in the polymerization reaction. Preferably, at least one of $R^1$ and $R^2$ includes a protected amine or an activated ester (i.e., one that reacts under mild conditions without necessitating coupling agents, such as HATU (O-(7-azabenzotriazol-1-yl)-1,1,3,3-tetramethyluronium hexaflourophosphate.

Figure 4:
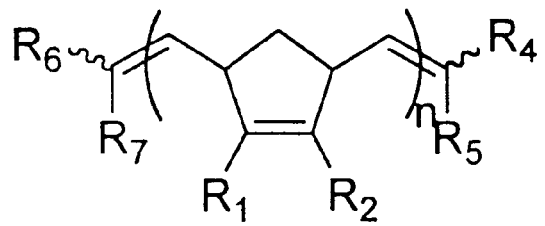
FIG. 4: Examples of polymer templates that can be prepared by methods of the present invention.
Figure 4:
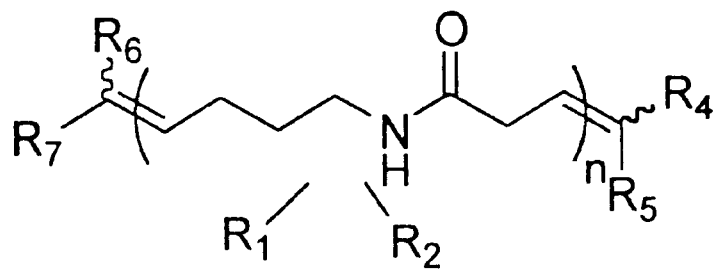
Figure 4:
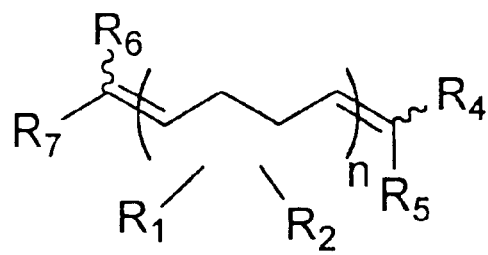
Figure 4:
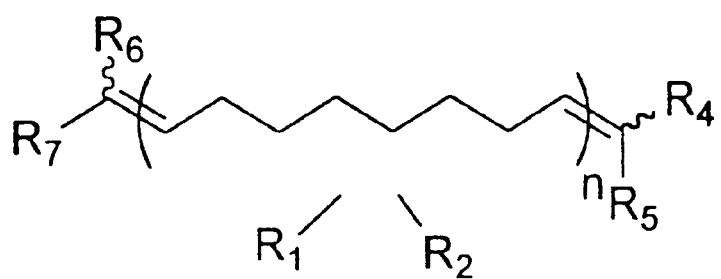

Examples of polymer templates having different backbones are illustrated in FIG. 4. A preferred example of the polymer template based on the norbornene template has the following general structure:

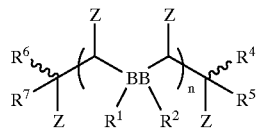

Formula III wherein Y, $R^1$, $R^2$, $R^4$, $R^5$, $R^6$, $R^7$, and n are as defined above. Preferably, at least one of $R^1$ and $R^2$ includes a protected amine or an activated ester. A preferred such polymer template is shown in FIG. 2 as Compound 3. Preferably, at least one of $R^4$, $R^5$, $R^6$, and $R^7$ includes functionality derived from a functionalized capping agent and/or a functionalized metal carbene catalyst, examples of which are described in Applicants' Assignee's U.S. Pat. No. 6,291,616, filed on even date herewith entitled "Methods and Reagents for Capping Ruthenium or Osmium Carbene-Catalyzed ROMP Products."

Another preferred example of the polymer template has the following general structure:

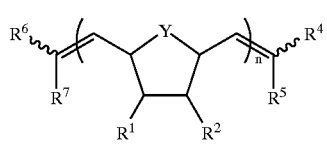

Formula IV wherein BB, $R^1$, $R^2$, $R^4$, $R^5$, $R^6$, $R^7$, and n are as defined above, and each Z is independently H, OH, SH, X (a halide such as F, Br, I, Cl), or $N(R^8)_2$ (wherein each $R^8$ is independently H or an organic group). Preferably, at least one of $R^1$ and $R^2$ includes a protected amine or an activated ester. Preferably, at least one of $R^4$, $R^5$, $R^6$, and $R^7$ includes functionality derived from a functionalized capping agent and/or a functionalized metal carbene catalyst, examples of which are described in Applicants' Assignee's U.S. Pat. No. 6,291,616, filed on even date herewith entitled "Methods and Reagents for Capping Ruthenium or Osmium Carbene-Catalyzed ROMP Products."

In the methods of the present invention, a pendant functional group is attached to the polymer template through latent reactive groups on the polymer template, which is derived from the monomer (e.g., activated ester groups). These latent reactive groups on the polymer template that are used for functionalization include electrophilic or nucleophilic groups, as discussed above. Similarly, the compounds from which the pendant functional groups are derived include electrophilic or nucleophilic groups, such that the respective reactive groups are matched to allow for reaction and attachment of the pendant functional group to the polymer template.

The functionalizing reagents (i.e., the compound from which the pendant functional group is derived) can include a wide variety of molecules that confer useful properties to the resultant polymer (e.g., biological activity), such as a carbohydrate or a peptide, for example. Thus, the pendant functional groups may provide a recognition element (i.e., binding site) for a biological entity, such as a cell surface receptor. Alternatively, they may be generally unreactive (e.g., nonbinding to a cell surface receptor). The polymer may include combinations of such groups. For example, a polymer can include alternating blocks of a recognition element and an unreactive element.

The methods of the present invention involve standard coupling techniques between functionalizing reagents and polymer templates, which may or may not be isolated prior to reaction. These coupling techniques will depend on the reactive groups selected and may involve solution, wherein the choice of solvent would depend on the type of reaction, or solid state reaction conditions depending on the solubility of the polymer template. Such techniques and conditions could be readily determined by one of skill in the art.

In the definitions of "R" groups as used herein, the term "organic group" means a hydrocarbon group (with optional elements other than carbon and hydrogen, such as oxygen, nitrogen, sulfur, and silicon, which can be in the form of various functional groups) that is classified as an aliphatic group, cyclic group, or combination of aliphatic and cyclic groups (e.g., alkaryl and aralkyl groups). In the context of the present invention, the organic groups are those that do not interfere with the formation of the polymer template or resultant polymer, unless they include the requisite reactive groups. The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon—carbon double bonds, such as a vinyl group. The term "alkynyl group" means an unsaturated, linear or branched hydrocarbon group with one or more carbon—carbon triple bonds. The term "cyclic group" means a closed ring hydrocarbon group that is classified as an alicyclic group, aromatic group, or heterocyclic group (which may or may not be aromatic). The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

Substitution is anticipated on the organic groups of the complexes of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy (ROH), alkoxy (ROR'), alkylsulfonyl ($RSO_2R'$), halogen atoms (F, Cl, Br, I), cyano (RCN), nitro ($RNO_2$), amino (primary $RNH_2$; secondary RR"NH or $R_2$NH; tertiary RR'R"N or $R_2$R"N or $R_3$N), carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

For the structures illustrated herein, for each R group that can include an organic group, which can be of a significantly large size, for example, on the order of 10,000 carbon atoms, the following applies. Preferably, the organic groups of $R^1$ and $R^2$ are each independently a $C_1$–$C_{5000}$ organic group, more preferably, $C_1$–$C_{2500}$ organic group, even more preferably $C_1$–$C_{1000}$ organic group, and most preferably, $C_1$–$C_{100}$ organic group, encompassing peptides, proteins, carbohydrates, metal chelators, natural products, etc. Preferably, the organic groups of $R^4$, $R^5$, $R^6$, and $R^7$ are each independently a $C_1$–$C_{10,000}$ organic group, more preferably, $C_1$–$C_{6000}$ organic group, even more preferably $C_1$–$C_{1000}$ organic group, and most preferably, $C_1$–$C_{500}$ organic group, encompassing antibodies, nucleic acids, peptides, proteins, carbohydrates, metal chelators, fluoresent tags, enzymes, solid supports, etc. Preferably, the organic groups of $R^3$ and $R^8$ are each independently a $C_1$–$C_{20}$ organic group, more preferably, $C_1$–$C_{10}$ alkyl group, and most preferably $C_1$–$C_3$ alkyl moiety.

In a specific example shown in FIG. 2, the functionalizing reagent is a carbohydrate substituted with a nucleophilic primary amine as the reactive group. The carbohydrate can be a neutral carbohydrate (e.g., galactose) or an anionic derivative (sulfated galactose residues). To react with the amine, the polymer template includes an activated ester group. Alternatively, however, the amine could be on the polymer template and the activated ester on the functionalizing reagent.

As an example, an amine-containing carbohydrate recognition element (e.g., a mannose derivative having an agly-cone linker terminating in a primary amine such as Compound 4 in FIG. 2) is reacted with an activated ester-containing polymer template (e.g., an NHS-substituted polymer template such as Compound 3 in FIG. 2) in an organic solvent (e.g., dimethylformamide, DMF) in the presence of a base (e.g., N-methylmorpholine, NMM) to remove excess acid with stirring at room temperature. If desired, a carbodiimide coupling agent, such as diisopropylcarbodiimide (DIC) can be included in this amide bond-forming step to enhance the efficiency of this linking (i.e., attachment) step and to enhance the yield of the desired post-synthetically modified (PSM) multivalent polymer product, which can be isolated and purified by a variety of techniques (e.g., dialysis, chromatography, precipitation, etc.) well known to those of skill in the art.

In a preferred embodiment, to minimize the possibility that nonspecific electrostatic effects would interfere with subsequent biological assays, the resulting polymer can be treated with a reagent that modifies acid groups that could be generated by side reaction of the activated esters, such as trimethylsilyldiazomethane to convert any unreacted free acid groups into methyl esters or ammonium hydroxide to generate primary amides. For this series of reactions, the specific conditions are set forth in the examples. For attachment of other pendant functional groups to other polymer templates using other latent reactive groups, one of skill in the art can readily determine the conditions (e.g., temperature, time, atmosphere) needed without undue experimentation.

The polymer templates can be provided in a kit, with or without functionalizing reagents, but with instruction means for attachment of the pendant functional groups, and optionally, the reagents needed for the attachment. The instructions will depend on the latent reactive groups present on the polymer templates. The kits could also include capping agents for functionalizing a terminus of a polymer chain. Examples of such capping agents are described in Applicants' Assignee's copending patent application U.S. patent application Ser. No. 09/336,121, filed on even date herewith entitled "Methods and Reagents for Capping Ruthenium or Osmium Carbene-Catalyzed ROMP Products."

Typically, the capping agent has the following general structure:

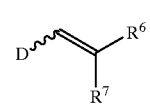

Figure 3:
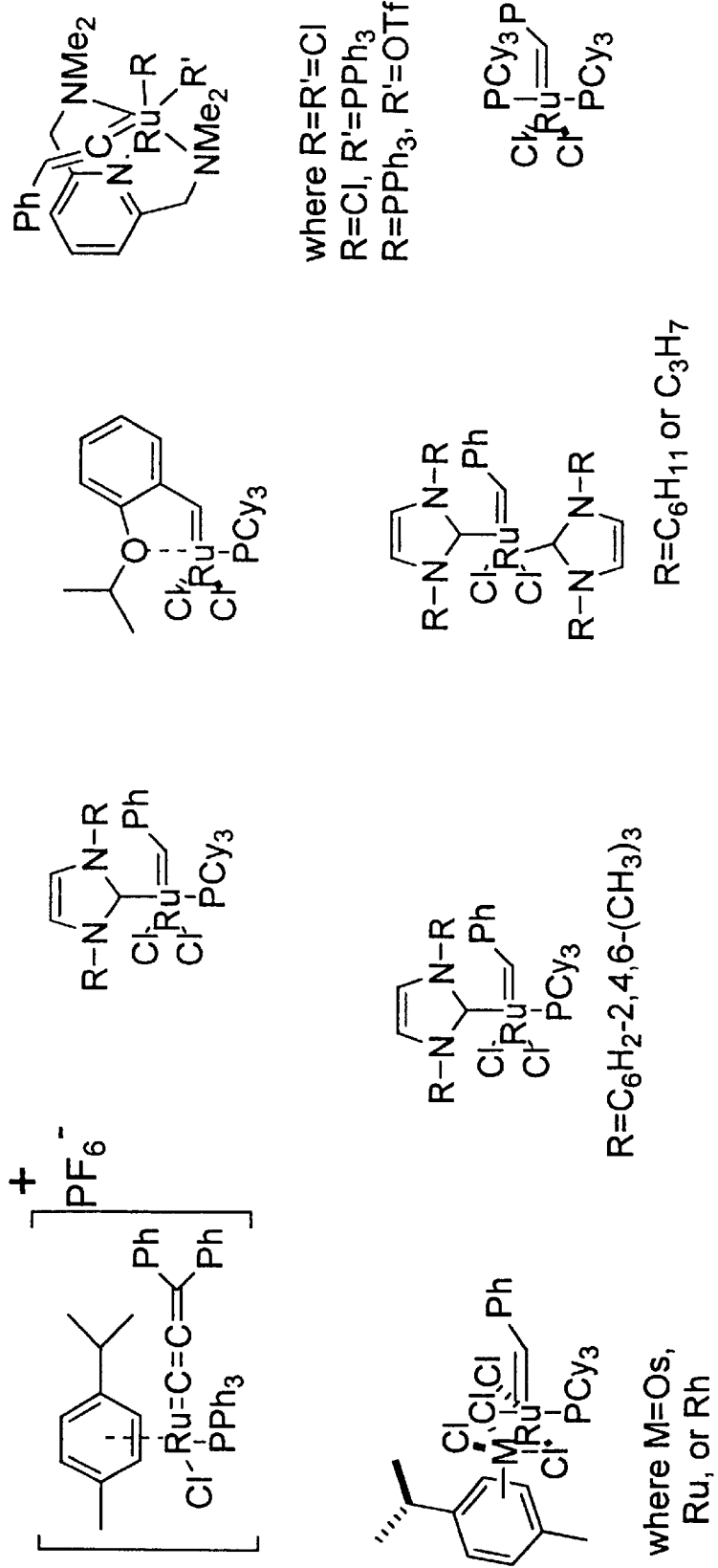
FIG. 3: Examples of metal carbene catalysts suitable for use in the present invention.

Formula V wherein D is an electron donating group (i.e., one that causes an overall increase in olefin electron density when compared to ethylene), D which can include $SR^9$, $OR^9$, halogen, where $R^9$ is a $C_1$–$C_{20}$ organic group, more preferably a $C_1$–$C_{10}$ alkyl group and most preferably a $C_1$–$C_3$ alkyl moiety, $R^6$ and $R^7$ are each independently H or an organic group, at least one of which preferably includes a latent reactive group or a nonreactive functional group that does not require further functionalization. Although both $R^6$ and $R^7$ can include functionality, preferably, only one does, and more preferably, the other is H. In one preferred embodiment, $R^6$ can include a latent reactive group selected from an azide, a nitro group, a disulfide, a hydrazine, a hydrazide, a hydroxylamine, an aldehyde, a ketone, an epoxide, a cyano group, an acetal, a ketal, a carbamate, a thiocyanate, an activated ester, or an activated acid. Alternatively, in another preferred embodiment $R^6$ can be a nonreactive functional group that is selected from natural products or analogs thereof (e.g., biotin), metal chelators (such as nitrilotriacetic acid), metals (such as Zn), fluorescent probes (such as an amide derived from BODIPY FL EDA which is 4,4-difluoro-5,7-dimethyl-4-bora-3a,4a-diaza-s-indacene-3-propionyl ethylenediamine), solid supports (such as polyethylene resins), and metal surfaces (such as gold surfaces used for surface plasmon resonance (SPR)). Examples of capping agents containing reactive functional groups are illustrated in FIG. 3 and examples of capping agents containing nonreactive functional groups are illustrated in FIG. 4.

Certain preferred capping agents include both latent or nonreactive functional groups and ethylene glycol groups. Typically, these both form a part of one or $R^6$ or $R^7$. A particularly preferred example of the capping agent includes an alkyl vinyl ether linked to a protected carboxylic acid derivative via an ethylene glycol chain. Because of its design, this linker minimizes nonspecific interactions with proteins or hydrophobic molecules.

Figure 5:
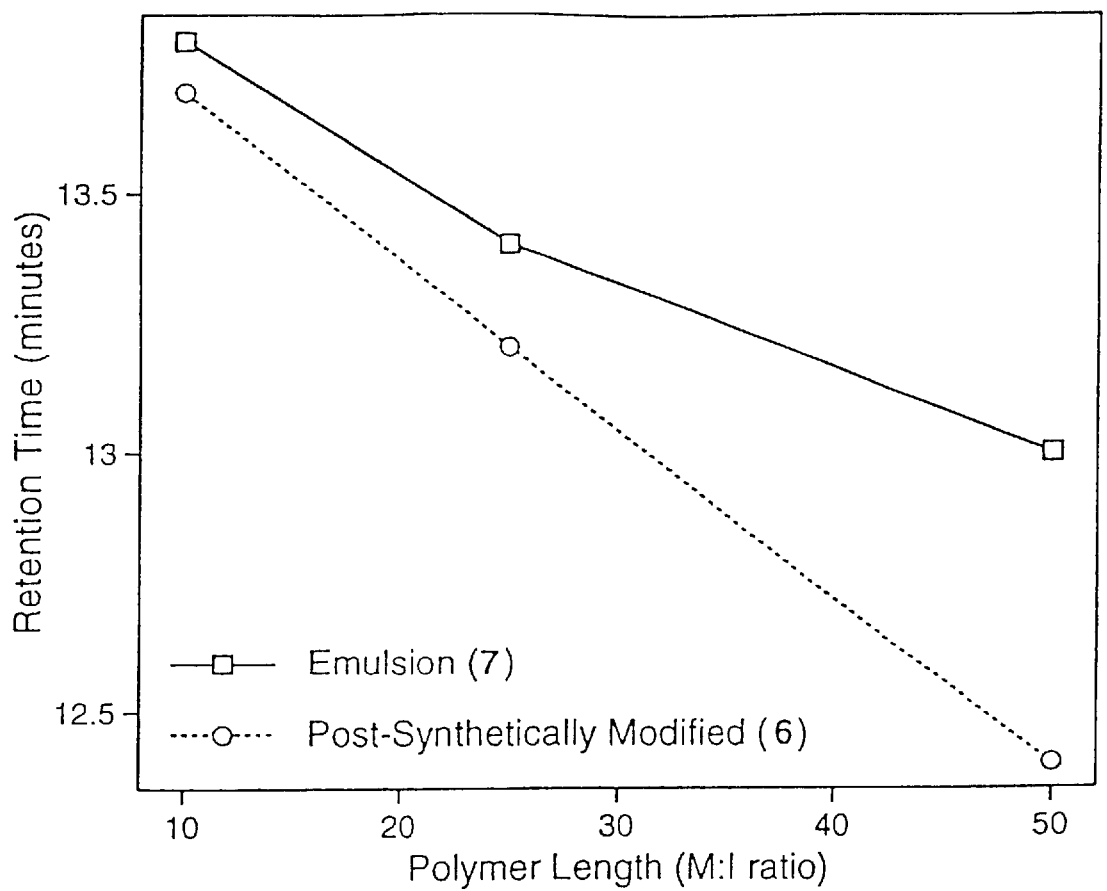
FIG. 5: GPC data shows that while the results from each polymerization are internally consistent, the emulsion polymerization conditions (Route B in FIG. 2) yield polymers of shorter relative length than the post synthetic modification conditions (Route A in FIG. 2).

To demonstrate the utility of the post-synthetic modification strategy of the method of the present invention, a series of NHS-substituted materials differing in average length (degree of polymerization, DP) using three monomer to initiator ratios (10:1, 25:1, and 50:1) were prepared (Reaction Path A, FIG. 2). All polymerization reactions proceeded efficiently, consuming all of the monomer. The mannose epitopes were appended by treatment of the activated oligomer backbones with amine to afford an oligomer series. Analogous materials were generated by the conventional method under emulsion polymerization conditions employing the same monomer to ROMP catalyst ratios (Reaction Path B, FIG. 2). No variations in the macroscopic physical properties of the oligomers prepared by the two methods were detected, and no differences were observable by $^1$H NMR spectroscopy. These results indicate the PSM procedure is efficient. The relative lengths of the materials generated by each method were assessed using gel permeation chromatography (GPC). The carbohydrate polymers 6 and 7 (FIG. 2) were acetylated to convert them into organic soluble derivatives, which can be more easily evaluated by GPC. Analyses of the materials suggested that the polymers generated under emulsion conditions are slightly shorter than those produced by post-polymerization modification (FIG. 5). Each method, however, provides a linear correlation between polymer length and monomer to initiator (M:I) ratios, an indication that the polymerization reactions are living. Thus, the PSM protocol according to the present invention can be used to prepare multivalent assemblies varying in length. The GPC data also suggests that the shortest polymers made by each method are within about 3 units length of one another, while the longest polymers are within about 12 units. The discrepancy in the lengths of the emulsion and PSM polymers highlights the differences in physical properties of the monomers that give rise to variations in the polymerization reaction. The new PSM procedure of the present invention is important because a wide range of different recognition elements can be attached to a single scaffold to give rise to materials with identical backbones. Such substances will facilitate the determination of structure/function relationships.

The method of the present invention was further investigated by comparing the biological activity of oligomers derived from the new process to those made by the conventional approach. The mannose-substituted polymers were designed to interact with the well-studied lectin Concanavalin A (Con A) (Goldstein, et al., Chapter 4, "Carbohydrate Binding Specificity of Concanavalin A"; in *Concanavalin A as a Tool,* H. Bittiger and H. P. Schnebli, Ed.; John Wiley & Sons, Ltd.: London, 1976; Coll., pp 55–65). Con A is a homotetramer at pH 7 that can facilitate the agglutination of red blood cells via simultaneous interactions with mannose residues on the surfaces of different cells. The ability of soluble carbohydrate ligands to inhibit cell agglutination can be measured. The efficacies of ROMP-derived oligomers in a Con A inhibition assay depend on their lengths (Kanai et al., *J. Am. Chem. Soc.,* 119, 9931–9932 (1997); and Mann et al., *J. Am. Chem. Soc.,* 120, 10575–10582 (1998)). Hemagglutination assays (Osawa et al., *Methods Enzymol.,* 28, 323–327 (1972)), therefore, provide a convenient format to assess the activities of materials generated from the two distinct preparation methods.

Figure 6:
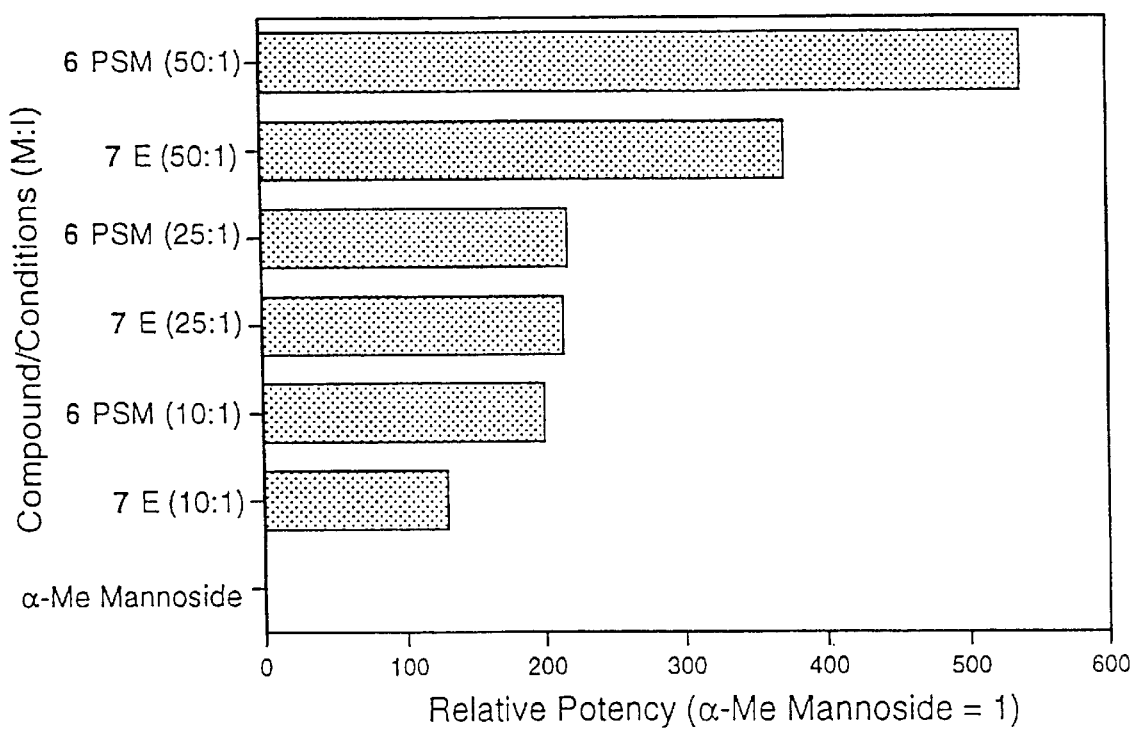
FIG. 6: Dependence of hemagglutination inhibition on polymer length. $IC_{50}$ values are reported (on a per saccharide basis). Potency was determined relative to α-methyl mannose. The results are the average of a minimum of five experiments, and the error associated with the dose determination is a factor of two, as dictated by the two fold dilutions in the assay. PSM stands for the post synthetic modification conditions of Route A in FIG. 2, and E represents the emulsion conditions of Route B in FIG. 2.

The Con A inhibitory potencies of different materials generated by the conventional and PSM protocols were compared on a saccharide residue basis using monovalent α-methyl mannopyranoside as a standard. Within a single series, either polymers 6 or 7, the most potent oligomers were those produced using a 50:1 monomer to initiator ratio (FIG. 6). This result is consistent with previous studies, which revealed that the most potent inhibitors are those that can span two saccharide binding sites on Con A (Kanai et al., *J. Am. Chem. Soc.,* 119, 9931–9932 (1997); and Mann et al., *J. Am. Chem. Soc.,* 120, 10575–10582 (1998)). At each M:I ratio, the PSM oligomers were slightly more active than those prepared under emulsion conditions. For example, a 400-fold increase over (x-methyl mannopyranoside was seen for the polymer derived from the 50:1 monomer-to-initiator ratio in the emulsion polymerization, but an enhancement of 550-fold was found for the related material made under post-polymerization modification conditions. The magnitude of effects seen with the previously studied norbornene imide mannose polymers was greater than those seen here. The present results are similar to those seen for the reduced norbornene imide mannose polymers. This may be due to a higher entropic cost in the orientation of the current backbone, which is less rigid than the bicyclic norbornene imide template. Because longer oligomers are more active inhibitors, this finding is consistent with the GPC data that indicates the average length of the PSM oligomer exceeds that of the material generated under the emulsion polymerization conditions. Overall, these data indicate that the PSM protocol can be used to synthesize biologically active materials with potencies that match or surpass those resulting from substances generated by standard ROMP approaches.

Objects and advantages of this invention are further illustrated by the following examples, but the particular materials and amounts thereof recited in these examples, as well as other conditions and details, should not be construed to unduly limit this invention.

EXAMPLES

Reactions were carried out in oven-dried glassware under nitrogen atmosphere, except as otherwise noted. ACS grade 1,2-dichloroethane (DCE) was used as received from Aldrich Chemical Co., Milwaukee, Wis. Solvents used in polymerization reactions were deoxygenated with a minimum of three freeze-pump-thaw cycles prior to use. Distilled, deionized (dd or MQ) water and 500 MWCO dialysis tubing (Fisher Scientific, Pittsburgh, Pa.) were used for the polymer purification. Chromatography solvents were ACS grade; dichloromethane, acetone and hexanes were distilled. Dodecyltrimethylammonium bromide (DTAB) was recrystallized from acetone. Analytical thin layer chromatography (TLC)

was performed on 0.25 mm precoated silica gel plates (60F-254 obtained from VWR, So. Plainfield, N.J.), and flash chromatography on silica gel (230–400 mesh, Scientific Adsorbents Inc., Atlanta Ga.). Visualization of TLC was done with ultraviolet light and p-anisaldehyde stain (15 mL p-anisaldehyde, 10 mL acetic acid, 10 mL sulfuric acid, and 350 mL ethanol). $^1$H and $^{13}$C NMR spectra were recorded on 300 or 500 MHz spectrometers; chemical shifts are reported downfield from tetramethylsilane in parts per million (δ). NMR solvents were obtained from Cambridge Isotope Laboratories, Inc., Andover, Mass. $^1$H NMR data are assumed to be first order with apparent doublets and triplets reported as d and t, respectively. Resonances that appear broad are designated as br.

Preparation of Bicyclo[2.2.1]hept-5-ene-exo-2-carboxylic acid N-hydroxysuccinimide ester, Compound 1 in FIG. 2: Norbomene acid (151.8 mg, 1.1 mmol, prepared according to the method of Ver Nooy et al., *J. Am. Chem. Soc.*, 77, 3583–3586 (1955)), N-hydroxysuccinimide (172.5 mg, 1.49 mmol, obtained from Aldrich), and EDCI (1-(3-dimethylaminopropyl)-3-ethylcarbodiimide hydrochloride, 278.1 mg, 1.45 mmol, obtained from Aldrich) were stirred in $CH_2Cl_2$ (3.6 mL, obtained from Aldrich) overnight under nitrogen. The solvent was removed under reduced pressure and the residue was subjected to flash silica gel chromatography with $CH_2Cl_2$ as the solvent according to the procedure of Still, *J. Org. Chem.*, 43, 2923 (1978). A white solid was isolated (186.7 mg, 0.88 mmol). Yield 80%. $^1$H NMR (300 MHz, CDCl$_3$): δ 6.19 (dd, J=5.7, 2.9 Hz, 1H), 6.17 (dd, J=5.7, 3.1 Hz, 1H), 3.25 (br s, 1H), 2.98 (br s, 1H), 2.82 (d, J=1.65 Hz, 2H), 2.49 (ddd, J=10.48, 4.78, 1.65 Hz, 1H), 2.03 (ddd, J=1 1.95, 4.23, 4.2 Hz, 1H), 1.55–1.41 (m, 3H). EI m/z 235.01847 [235.2395, calc'd for $C_{12}H_{13}NO_4$].

Polymerization of bicyclo[2.2.1]hept-5-ene-exo-2-carboxylic acid N-hydroxysuccinimide ester, Compound 3 in FIG. 2 (n=10): The N-hydroxy ester (98.3 mg, 0.425 mmol) 1 was dissolved in 1,2-dichloroethane (DCE) (2.1 mL). To this was added a solution of $[(Cy)_3P]_2Cl_2Ru=CHPh$ (Strem, Newburyport, N.H.) in deoxygenated DCE (35 mg in 2.1 mL). The reaction was stirred under nitrogen at room temperature for forty-five minutes. The reaction appeared complete by TLC, and an excess of ethyl vinyl ether was added for capping. The reaction mixture was filtered through a small plug of silica gel using $CH_2Cl_2$ as eluent. The solvent was removed under reduced pressure to afford a brown solid (96.8 mg) that was used without further purification. Yield 98%. $^1$H NMR (300 MHz, CDCl$_3$): δ 7.3 (m), 5.7–5.2 (m), 3.5–0.90 (br m).

Preparation of aminoethyl-α-D-mannopyranoside, Compound 4, FIG. 2: The azidoethyl mannoside was prepared according to the procedure of Chernyak et al., *Carbohyd. Res.*, 225, 279–289 (1992) with minor modifications. Azidoethanol was substituted for allyl alcohol and glycosylation conditions were used as described by Lee et al., *Carbohyd. Res.*, 37, 193–201 (1974). The azidoethyl mannoside was reduced with Pearlmann's catalyst (Aldrich) in a 1:1 mixture of methanol:water (a modification of a procedure mentioned above) to give 4.

Preparation of aminoethyl-α-D-mannopyranosyl bicyclo[2.2.1]hept-5-ene-exo-2-carboxamide, Compound 5, FIG. 2: The mannose monomer 5 was prepared via the pentafluorophenyl ester and Compound 4 by a procedure previously described in Manning et al., *Tetrahedron*, 53, 11937–11952 (1997). $^1$H NMR (300 MHz, D$_2$O): δ 6.19 (dd, J=5.7, 2.9 Hz, 1H), 4.694 (d, J=1.65 Hz, 1H), 3.76 (dd, J=2.94, 1.83, 1H), 3.70 (dt, J=12.32, 1.9 Hz, 1H), 3.64–3.41 (m, 6H), 3.29 (br m, 1H), 2.76 (br m, 1H), 2.03 (m, 1H), 1.57 (m, 1H), 1.35–1.17 (m, 3H). EI m/z 343.1627 [343.377, calc'd for $C_{16}H_{25}NO_7$].

Coupling to product of the polymerization of bicyclo[2.2.1]hept-5-ene-exo-2-carboxylic acid N-hydroxysuccinimide ester, Compound 6 in FIG. 2 (n=10): Aminoethyl mannoside 4 (16.0 mg, 0.0788 mmol), N-methylmorpholine (7.7 μL, 0.0702 mmol, Aldrich) and polymer 3 (n=10, 15.2 mg, 0.0647 mmol) in 0.35 mL dimethyl formamide (DMF) were stirred for 24 hours. Diisopropylcarbodiimide (DIC, 11 μL, 0.0638 mmol, Aldrich) was added and stirring continued overnight. The DMF was removed under reduced pressure, and the resulting solid was washed three times with 1–2 mL of $CH_2Cl_2$ and three times with 1–2 mL of ethanol. The solid was dried, and (trimethylsilyl)diazomethane (TMSCHN$_2$, 35 μL, 0.0702 mmol, Aldrich) and methanol (350 μL) were added and the reaction stirred overnight. The reaction was quenched upon addition of water, and the solvent was removed under reduced pressure. The solid was dissolved in MQ water and placed in dialysis tubing. The sample was dialyzed (48 hours, four water changes, 1 L each time) to remove impurities from the coupling reaction and unreacted 4. The solution was filtered through a 0.25 micron filter and the solvent was removed under reduced pressure to give a tan solid (15.4 mg, 71%). $^1$H NMR (300 MHz, D$_2$O): δ 7.3 (br m, 0.278H), 5.5–4.9 (br, 2H), 4.0–3.0 (br m, 14H), 2.5–2.15 (br m, 2H), 1.9–1.4 (br, 2H), 1.1–0.9 (br, 2H).

Polymerization of aminoethyl (c-D-mannopyranosyl bicyclo[2.2.1]hept-5-ene-exo-2-carboxamide, Compound 7 in FIG. 2 (n=10): The mannose monomer 5 (19.6 mg, 0.0571 mmol) and DTAB (dodecyltrimethylammonium bromide, 29 mg, 0.0933 mmol, Aldrich) were dissolved in water (182 μL) and degassed. DCE (181 μL) was added to the ruthenium catalyst 2 (6.1 mg) and this solution (91 μL corresponding to 4.7 mg, 0.00571 mmol of 2) was added to the solution of 5. The reaction was stirred at room temperature for thirty minutes and then was heated to 60° C. for 4 hours. Once the reaction was complete by TLC, an excess of ethyl vinyl ether was added to quench the active carbene. The reaction mixture was evaporated under reduced pressure, and the solid was washed with dichloromethane and ethanol. The polymer was dissolved in MQ water and dialyzed against 1 L of water for 2 days, changing the water every 12 hours. The solution was removed from the dialysis tubing and filtered through a 0.25 micron filter which after removal of the solvent under reduced pressure gave a tan solid (18.2 mg). Yield 90%. $^1$H NMR (300 MHz, D$_2$O): δ 7.3 (br m, 0.238H), 5.5–4.9 (br, 2H), 4.0–3.0 (br m, 14H), 2.5–2.15 (br m, 2H), 1.9–1.4 (br, 2H), 1.1–0.9 (br, 1H).

Hemagglutination Assay: This assay was performed as previously described in Kanai et al, *J. Am. Chem. Soc.*, 119, 9931–9932 (1997) and references therein. The concentrations of the polymer samples used in the assay were determined by $^1$H NMR integration of the peak at 5.25 ppm with an external sample of NaOAc of known concentration.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A polymer template having the following general structure:

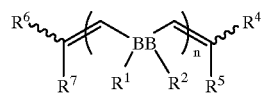

Formula II wherein "BB" represents the backbone repeat unit, which may be cyclic or acyclic, and may be the same or different in a random or block arrangement, $R^1$ and $R_2$ are each independently H or an organic group, which may be connected such that they form a ring, with the proviso that at least one of $R^1$ and $R^2$ includes a protected amine or an activated ester, $R^4$, $R^5$, $R^6$, and $R^7$ is H or an organic group, and n is the average number of repeating monomer units.

2. The polymer template of claim 1 wherein n is at least 2.

3. The polymer template of claim 1 wherein at least one of $R^4$, $R^5$, $R^6$, and $R^7$ includes a functional group.

4. A polymer template having the following general structure:

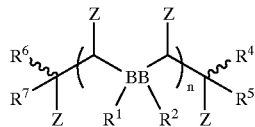

Formula III wherein "BB" represents the backbone repeat unit, which may be cyclic or acyclic, and may be the same or different in a random or block arrangement, $R^1$ and $R^2$ are each independently H or an organic group, which may be connected such that they form a ring, with the proviso that at least one of $R^1$ and $R^2$ includes a protected amine or an activated ester, $R^4$, $R^5$, $R^6$, $R^7$ is H or an organic group, Z is independently hydrogen, a halide, hydroxyl, a thiol, or an amine, and n is the average number of repeating monomer units.

5. The polymer template of claim 4 wherein at least one of $R^4$, $R^5$, $R^6$, and $R^7$ includes a functional group.

* * * * *

UNITED STATES PATENT AND TRADEMARK OFFICE
CERTIFICATE OF CORRECTION

PATENT NO. : 6,538,072 B2
DATED : March 25, 2003
INVENTOR(S) : Kiessling et al.

It is certified that error appears in the above-identified patent and that said Letters Patent is hereby corrected as shown below:

Column 6,
Line 63, please delete "RR'NH" and replace it with -- RR"NH --.
Line 65, please delete "$(R_2RSO_2$" and replace it with -- $(R_2SO_2$ --.

Column 11,
Line 31, please delete "$R_2R"N$" and replace it with -- $R_2R'N$ --.

Column 15,
Line 22, please delete "30".

Column 16,
Line 27, please delete "(c-D-mannopyranosyl" and replace it with
-- α-D-mannopyranosyl --.

Signed and Sealed this

Ninth Day of September, 2003

JAMES E. ROGAN
*Director of the United States Patent and Trademark Office*